United States Patent
Toone et al.

(10) Patent No.: US 8,598,368 B2
(45) Date of Patent: Dec. 3, 2013

(54) STABLE NEUTRAL NITRIC OXIDE SOURCE

(75) Inventors: Eric J. Toone, Durham, NC (US); Harinath Chakrapani, Maharashtra (IN)

(73) Assignee: Duke University, Durham, NC (US)

( * ) Notice: Subject to any disclaimer, the term of this patent is extended or adjusted under 35 U.S.C. 154(b) by 448 days.

(21) Appl. No.: 12/532,918

(22) PCT Filed: Apr. 16, 2008

(86) PCT No.: PCT/US2008/004904
§ 371 (c)(1),
(2), (4) Date: Jan. 28, 2010

(87) PCT Pub. No.: WO2008/130567
PCT Pub. Date: Oct. 30, 2008

(65) Prior Publication Data
US 2010/0184992 A1    Jul. 22, 2010

Related U.S. Application Data

(60) Provisional application No. 60/907,877, filed on Apr. 20, 2007.

(51) Int. Cl.
*C07D 498/08* (2006.01)

(52) U.S. Cl.
USPC .......................................... 548/241

(58) Field of Classification Search
USPC ................................. 548/242, 241
See application file for complete search history.

(56) References Cited

U.S. PATENT DOCUMENTS 7,049,308 B2 * 5/2006 Stamler et al. ........... 514/211.07

* cited by examiner

*Primary Examiner* — Kristin Vajda
(74) *Attorney, Agent, or Firm* — Bacon & Thomas, PLLC

(57) ABSTRACT

C-nitroso compound capable of releasing neutral nitric oxide is made stable by forming a Diels Alder adduct thereof which is functionalized at the Diels-Alder double bond to impart the stability. Treatment of the stabilized adduct with agent that removes functionalization and regenerates Diels Alder double bond triggers delivery of neutral nitric oxide via retro Diels-Alder reaction and homolytic scission.

2 Claims, 1 Drawing Sheet

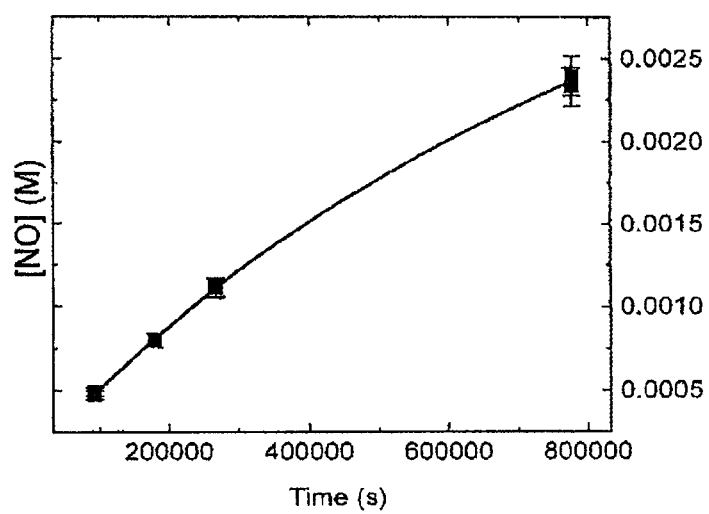

STABLE NEUTRAL NITRIC OXIDE SOURCE

TECHNICAL FIELD

This invention is directed to a stable compound which is capable of releasing neutral nitric oxide.

BACKGROUND OF THE INVENTION

Nitric Oxide (NO) donors are known to be useful for therapeutic utility, e.g., to prevent restenosis following angioplasty (Gloves, P., et al., Cardiovascular Research 26, 615-619 (1992)), to inhibit platelets to prevent coagulation and thrombus formation (Groves, P., et al., Circulation 87, 590-597 (1993)) and to treat angina (Knight, et al., Circulation 95, 125-132 (1997)). NO donors are considered to have additional therapeutic utility in cancer, killing microbes and viruses, relaxing airways and intestinal smooth muscle (e.g., for treating asthma and esophageal spasms), in promoting erectile function and in treatment of heart failure and urinary incontinence.

Nitric oxide can exist in three forms, namely in the oxidized form as nitrosonium ion ($NO^+$), as neutral nitric oxide (the stable free radical NO.) and in the reduced form as nitroxyl ion ($NO^-$).

The three forms are considered to have different physiological functions.

Administration of nitrosonium ion is favored for signaling receptors. The C-nitroso compounds that are the subject of the following set of patents where one of the inventors herein is a co-inventor, donate nitric oxide in the form of nitrosonium ion: see U.S. Pat. Nos. 6,359,182; 6,538,116; 6,887,994; 7,030,238 and 7,049,308. These C-nitroso compounds generate nitrosonium instead of nitroxyl because the nitroso is derived from a carbon acid with relatively low pKa so that there is no beta proton acidic enough to cause beta elimination between the nitroso and the beta proton.

Administration of neutral nitric oxide is favored for vasodilation and to inhibit aggregation of platelets and functions by nitrosylating the iron moiety of heme or nitrosylating G-protein.

Administration of nitroxyl ions increases cardiac output and reduces venous output for treatment of heart failure and protects against reperfusion injury.

While donors of neutral nitric oxide are known, e.g., sodium nitroprusside, the known neutral nitric oxide donors are unstable and therefore have storage stability problems and/or are spontaneously converted to neutral nitric oxide, and because of the low stability, are only useful for treating acute conditions, e.g., hypertensive emergency and to decrease myocardial oxygen demand after acute myocardial infarction and to increase cardiac output in congestive heart failure or when short-term reduction of cardiac preload and/or afterload is desired.

It has been discovered herein that problems currently limiting the therapeutic use of neutral nitric oxide donors can be overcome by preparing compound that releases neutral nitric oxide in a second order reaction. As used herein, the term "second order reaction" means reaction where the reaction rate depends on the concentration of one reactant raised to the second power or the concentration of two different reactants each raised to the first power.

SUMMARY OF THE INVENTION

The invention herein in one embodiment is directed to a compound that requires second order reaction for release of neutral nitric oxide. The compounds are storage stable, that is, do not decompose to release nitric oxide over time or in light and are useful to treat, on activation by triggering, not only acute conditions but also chronic conditions, e.g., chronic hypertension and chronic coronary artery disease.

The invention in a second embodiment is directed to C-nitroso compound precursor for the compound of the first embodiment.

BRIEF DESCRIPTION OF THE DRAWING

FIG. 1 shows the graph from Working Example 1.

DETAILED DESCRIPTION

A compound of the first embodiment herein is a Diels-Alder adduct of a C-nitroso compound capable of releasing neutral nitric oxide which is functionalized to be stable and to require second order reaction for release of neutral nitric oxide.

The precursor for this compound, that is the precursor compound which is reacted to form the functionalized Diels-Alder adduct, is a C-nitroso compound which has a molecular weight ranging from 75 to 1,000, wherein a nitroso group is attached to a tertiary carbon and is obtained by nitrosylation of a carbon acid having a pKa greater than about 30, where the CH group of the carbon acid dissociates to C and H to provide a site for nitrosylation and contains a substituent on the carbon acid which provides a homolytic bond energy for nitroso below 35 kcal/mol without raising the acidity of the carbon acid to below 30.

As used herein the term "tertiary carbon" means a carbon atom singly bonded to three other carbon atoms.

If the nitroso group is not attached to a tertiary carbon, there is essentially irreversible tautomerization to the corresponding oxime which is generally not active.

The nitrosylation of a carbon acid having a pKa greater than about 30 is necessary for eventual release of neutral nitric oxide. If the carbon bearing the nitroso moiety is derived from a carbon acid with a pKa below about 30, the corresponding C-nitroso compound is a donor of nitrosonium.

The homolytic bond energy below 35 kcal/mol is necessary to allow decomposition to uncharged nitric oxide and uncharged residue (portion of compound remaining after uncharged nitric oxide is released). Substituent on tertiary carbon providing this bond energy is, for example, nitrile, acyl or aromatic substituent.

The precursor C-nitroso compound herein can be of the following types.

In a first case, the compound has a substituent Q which is attached to the tertiary carbon and which consists of a chain moiety containing from 0 to 12 chain atoms consisting of 0 to 10 carbon atoms, 0 to 5 nitrogen atoms and 0 to 5 oxygen atoms covalently bonded to a cyclic moiety which is monocyclic, bicyclic, tricyclic, tetracyclic or pentacyclic and contains 5 to 24 ring atoms consisting of 2 to 20 carbon atoms, 0 to 4 nitrogen atoms, 0 to 2 oxygen atoms and 0 to 2 sulfur atoms. When the chain moiety consists of no chain atoms, the cyclic moiety is covalently bonded to the tertiary carbon.

In a second case, the tertiary carbon is a ring atom in a cyclic moiety which is monocyclic, bicyclic, tricyclic, tetracyclic or pentacyclic and contains from 5 to 24 ring atoms consisting of 2 to 20 carbon atoms, 0 to 4 nitrogen atoms, 0 to 2 oxygen atoms and 0 to 2 sulfur atoms where the ring atoms are counted by counting the atoms forming the ring(s), and exclude hydrogen and any other substituent on the ring. In this case two of the carbon atoms attached to the tertiary carbon are part of the ring structure of the cyclic moiety.

In a third case, the C-nitroso compound is acyclic and at least one substituent on the tertiary carbon contains 4 to 20 carbon atoms.

An example of the second case is:

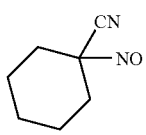

(1)

We turn now to the synthesis of the C-nitroso compounds for preparing the Diels-Alder adduct of the first embodiment herein.

Several methods applicable to synthesizing C-nitroso compounds are disclosed in Boyer, J. H., "Methods of Formation of the Nitroso Group and its Reactions" in The Chemistry of the Nitro and Nitroso Groups, Part 1, Feuer, H, Editor, John Wiley & Sons, New York (1969) at pages 215-299 and in Touster, O. in Organic Reactions, Vol. 7, John Wiley & Sons, New York (1955) at pages 327-377, and in Gowenlock, B. G., et al., Chem. Rev. 104 7, 3315-3340 (July 2004), which are incorporated herein by reference.

In a method useful for synthesizing C-nitroso compounds regardless of the acidity, the carbon acid is converted to the corresponding hydroxylamine which is oxidized, for example, using silver carbonate on Celite.

A very comprehensive article teaching methods applicable to synthesizing precursor c-nitroso compounds herein, is Gooden, D. M; Chakrapani, H., and Toone, E. T., Current Topics in Medicinal Chemistry 5(7), 687-705 (2005).

Diels-Alder adduct of precursor c-nitroso compound is formed by reaction of a linear or cyclic diene containing from 4 to 10 carbon atoms and precursor C-nitroso compounds. The dienophile moiety is the double bond of the nitroso group.

The preferred diene is cyclopentadiene. Other useful dienes include, for example, cyclobutylene, cyclohexadiene, cyclooctadiene, furan, butadiene, pentadiene, isoprene, and 2,4 and 1,5-hexadienes.

We turn now to reaction of diene and C-nitroso compound to form Diels Alder adduct of the precursor c-nitroso compound. The reaction is best carried out at room temperature or only slightly above it with excess diene in hydrocarbon solvent, e.g., benzene. If the C-nitroso compound is substituted with electron-withdrawing substituent(s), the reaction proceeds more easily than otherwise. The presence of electron-withdrawing substituents in the diene slows the reaction down, and the presence of electron-donating substituents in the diene speeds the reaction up.

An example of Diels-Alder adduct formation from compound 1 and cyclopentadiene is given below.

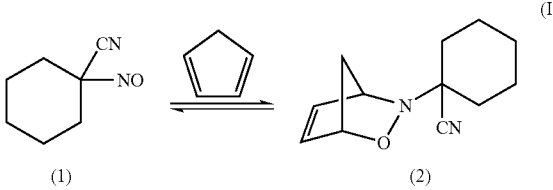

(I)

Functionalization to obtain stability and to require second order reaction for release of neutral nitric oxide is at the Diels-Alder double bond.

Functionalization to obtain stability and to require second order reaction for release of neutral nitric oxide is obtained, for example, by bromination, or by reaction with diethoxy-oxophosphoranesulfenyl chloride or by providing sulfone or sulfoxide at the double bond of (2). The functionalization causes the Diels-Alder reaction to become irreversible.

An example of bromination of the Diels-Alder adduct formed in reaction (I) above, is given below by reaction equation II (the brominated Diels-Alder adduct is denoted 4).

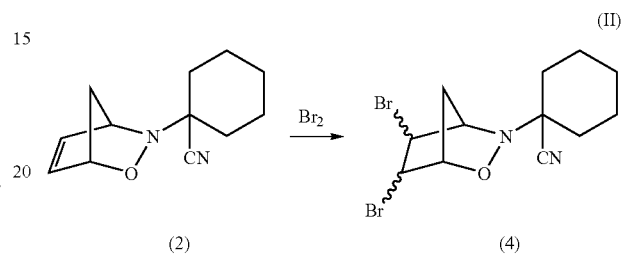

(II)

The reaction is demonstrated in Working Example I.

Examples of reaction of Diels-Alder adduct 2 with diethy-oxyoxophosphorane sulfenyl to form thiirane derivative (5) is set forth below.

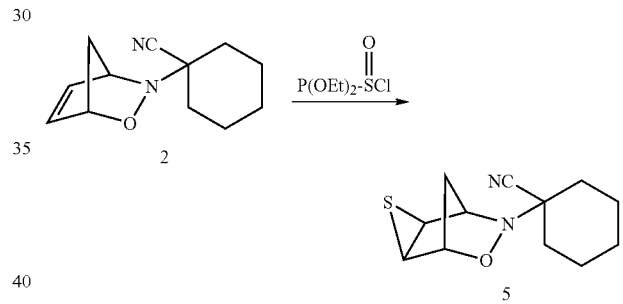

The reduction of (5) to provide (6) is set forth below.

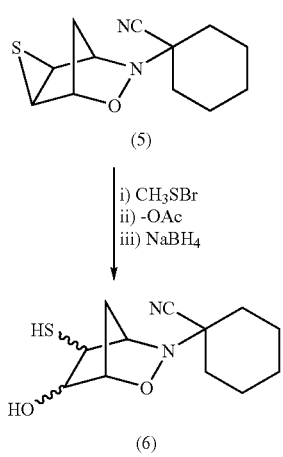

The reactions to produce (5) and (6) are demonstrated in Working Example II.

Compounds (4) and (6) react in blood to eliminate the functionalization to provide Diels-Alder adduct which is not functionalized. The elimination of functionalization constitutes the first step in a second order reaction. Thereupon retro Diels-Alder reaction (cycloreversion) occurs in seconds to provide the precursor C-nitroso compound, and then homolytic scission (decomposition into two uncharged atoms or radicals) occurring in seconds, releases neutral nitric oxide. An exemplary homolytic scission for compound 1 is

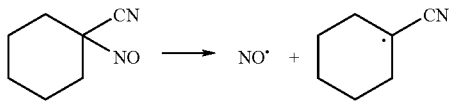

The release of neutral nitric oxide in blood in a second order reaction from compound 4, that is bromination functionalized Diels-Alder adduct, is caused by iodide in blood by elimination of bromine group by the iodide followed by retro Diels-Alder reaction and homolytic scission. The defunctionalization reaction involves iodide-promoted debromination of vicinal dibromides and regeneration of the double bond. Iodide would be present in blood of patients being treated with sodium iodide or kelp for hyperthyroidism or amiodarone for arrhythmia. The reactions are illustrated below:

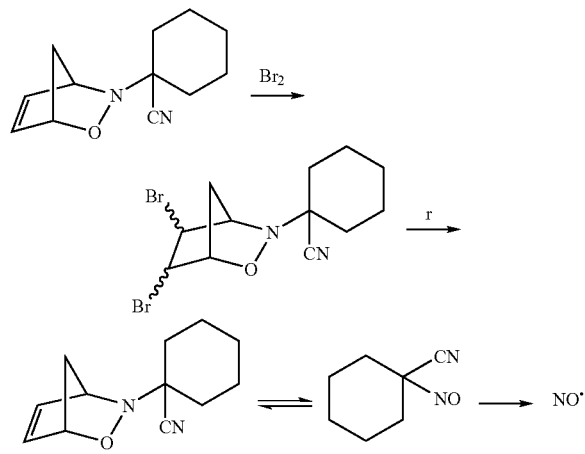

The release of neutral nitric oxide in blood in a second order from compound (6) is caused by oxygen in blood by oxidative elimination of thiol and hydroxy groups and regeneration of the Diels-Alder double bond followed by retro Diels-Alder reaction and homolytic scission.

The reactions are illustrated below:

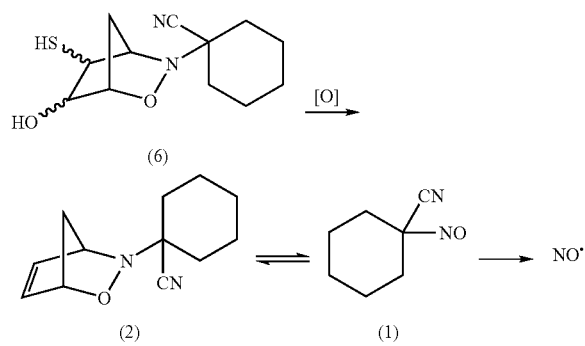

The oxygen is present in blood of patients.

The release of neutral nitric oxide in a second order reaction from (5) occurs by reductive elimination of thiirane and regeneration of the Diels-Alder double bond followed by retro Diels-Alder double bond followed by retro Diels-Alder and homolytic scission. The reductive elimination will occur in acidic milieu in the body, e.g., the stomach.

The bromine derivative is suitable for treating these patients if they have iodide present in blood as a result of therapy for a different disorder.

Dosages of functionalized Diels-Alder adduct range from 1 nanomolar to 100 micromolar concentration in blood. Route of administration is preferably intravenous. Other parenteral, inhaled, nebulized and topical routes of administration are also useful.

Elements of the invention and examples are set forth in Appendixes A and B hereto.

The invention is illustrated by the following working examples:

Working Example I

Formation of N-(1-Cyanocyclohexyl)bicyclo[2.2.1]4,5-dibromo-3,6-dihydro-1,2-oxazine 4 and activation thereof with iodide to release neutral nitric oxide.

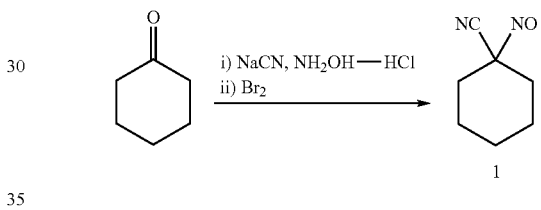

α-Cyano-C-nitroso compounds were synthesized from the corresponding ketone according to literature methods (Rehse, K.; Herpel, M. *Pharm. Med. Chem.* 1998, 331, 104-110; Gowenlock, B. G.; Pfab, J.; Kresze, G. *Leibigs Ann. Chem.* 1975, 1903-1913; Gregor, V. *Coll. Czech. Chem. Comm.* 1958, 23, 1782; DiStillo, A., Medana, C.; Ferrarotti, B.; Gasco, L; Ghigo, D.; Bosia, A.; Martorana, P. A.; Gasco, *A. Pharm. Res.* 2000, 41, 469-474).

Diel's Alder adduct 2 was formed from 1 as follows:

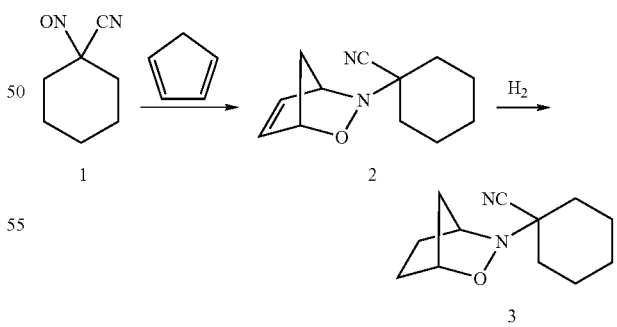

Treatment of 1 with excess cyclopentadiene in benzene at 25° C. resulted in loss of the characteristic blue color of the C-nitroso species. At 0° C., a white solid, presumed to be 2, precipitated from solution. On warming, the solid turned blue, suggesting retro Diels Alder reaction and re-generation of 1. To confirm the identity of 2, hydrogenation produced stable compound 3 as described below.

Hydrogenation of 2 forming N-(-1-cyanocyclohexyl)bicyclo[2.2.1]3,4,5,6-tetrahydro-1,2-oxazine 3 was carried out as follows: A solution of 2 (80 mg, 0.39 mmol) in ice cold methanol (5 mL) was hydrogenated (1 atm) with 10% Pd/C (5 mg). After 4 h, the reaction mixture was passed through celite, and washed several times with ether (50 mL). Removal of solvent under reduced pressure, followed by flash chromatography (silica gel, hexanes: ether) afforded 3 as a white solid in 44% yield. $^1$H NMR: δ 4.52 (s, 1H), 3.82 (s, 1H), 2.64̄2.61 (m, 1H), 2.16 (m, 1H), 1.91̄1.15 (m, 14H). $^{13}$C NMR: δ 121.9, 58.9, 35.1, 34.6, 30.9, 25.0, 22.3, 21.8. IR (film, cm$^{-1}$). 2241. Elemental analysis for $C_{12}H_{18}N_{20}$ calcd. (found), C, 70.08 (69.84); H, 9.08 (8.80); N, 13.25 (13.58).

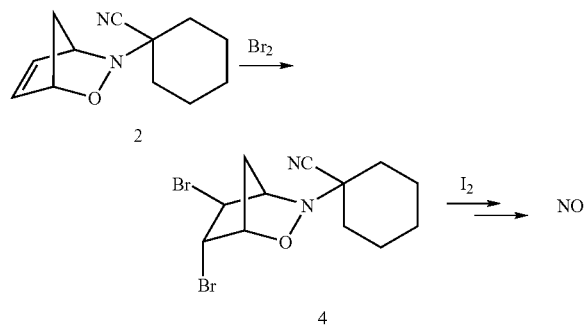

Bromination of 2 to produce N-(1-cyanocyclohexyl)bicyclo[2.2.1]4,5-dibromo-3,6-dihydro-1,2-oxazine 4 was carried out as follows: A solution of 2 (80 mg, 0.43 mmol) in dichloromethane under ice was treated with bromine (0.1 mL). Work up of the reaction mixture after 4 h, and flash chromatography (silica gel, hexanes, ether) afforded 35 mg (0.17 mmol) of 4 in 44% yield, as a mixture of diastereomers. $^1$H NMR: δ 4.52 (s, 1H), 3.82 (s, 1H), 2.64-2.61 (m, 1H), 2.16 (m, 1H), 1.91̄1.15 (m, 12H). $^{13}$C {$^1$H}NMR: δ 121.9, 58.9, 35.1, 34.6, 30.9, 25.0, 22.3, 21.8. IR (film, cm$^{-1}$): 2939, 2227, 1453. Elemental Analysis for $C_{12}H_{16}Br_2N_2O$: calcd. (found) C, 39.59 (40.44); H, 4.43 (4.44); N, 7.69 (7.33). HRMS calcd. (found): 361.9629 (361.9643). Melting pt. 114̄116° C.

Release of nitric oxide from 4 via 2 was obtained and shown as follows:

A nitric oxide analyzer was constructed constituted of a reservoir connected to a chemiluminescence-based detector.

Calibration was carried out as follows: Solutions of sodium nitrite of the concentrations 1 mM, 0.1 mM, 0.01 mM, 1 μM, 0.1 μM, 0.01 μM, and 1 nM, were freshly prepared before every experiment. The reservoir of the nitric oxide analyzer (NOA) was filled with 2-3 mL glacial acetic acid, and a steady stream of He was maintained. 50 mg of KI was dissolved in dionized water and added to the reservoir. After a few minutes, the reservoir was connected with the chemiluminescence-based detector. Solutions of nitrite are rapidly and quantitatively reduced to NO, which is then carried by the helium stream into the chemiluminescence spectrometer, in which free nitric oxide is detected by reaction with ozone. Calibration was done with successive injections starting from the least concentrated till the limits of detection were reached. A new calibration curve was generated for every experiment and performed with excellent linear fit (R=0.999).

Iodide activated release of nitric oxide from 4 was obtained as follows: Typical procedure for sample preparation is dissolving 4 (10 mg, 0.027 mmol) in 10 mL DMSO to obtain 2.7 mM solutions. To this, 45 mg KI (0.27 mmol, 10 eq.) was added, and the solution was divided into several portions (~0.2 mL). After the required time period at 25° C. or 37° C., the portions were analyzed for nitric oxide. The samples used for determining nitric oxide release were stored in the dark at 25° C. or at 37° C. in an incubator, for the mentioned time period in airtight vials. Blank injections of DMSO and KI in DMSO were performed before every experiment. The kinetics was studied by periodically measuring the amount of nitric oxide formed. A 5.4 mM solution of 4 at 25° C. was treated with 10 eq. KI and 2.7 mM solutions of 4 were treated with 25 eq. and 50 eq. KI at 25° C. Similarly a solution of 4 was treated with 25 eq. KI and placed in an incubator at 37° C.; periodically, samples were withdrawn and nitric oxide analysis in solution was carried out.

Plots were determined from the nitric oxide analysis in millivolts versus minutes.

Kinetics of nitric oxide release from 4 when treated with 50 eq. KI at 25° C. was determined to be as shown in FIG. 1.

Working Example II

Forming Compounds (5) and (6)

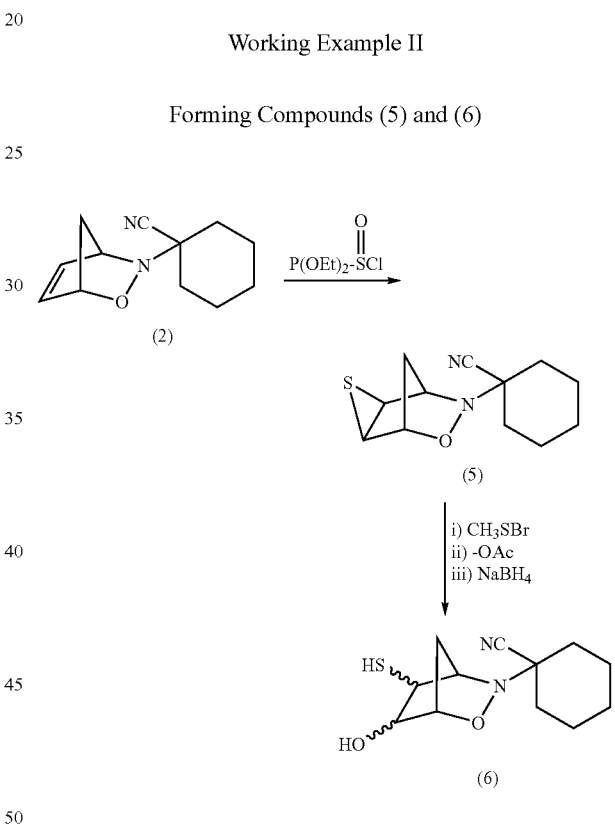

N-(1-Cyanocyclohexyl)bicyclo[2.2.1]4,5̃-thiirane-3,6-dihydro-1,2-oxazine (5): A solution of 3 (80 mg, 0.43 mmol) in DCM under ice was treated with diethoxyoxophosphoranesulfenyl chloride (0.1 mL). Work up of the reaction mixture after 4 h, and flash chromatography affords the corresponding thiirane, as a mixture of diasteromers.

N-(1-Cyanocyclohexyl)bicyclo[2.2.1]4-thio-5-hydroxy-3,6-dihydro-1,2-oxazine (6): A solution of N-(1-Cyanocyclohexyl)bicycle[2.2.1]4,5-thiirane-3,6-dihydro-1,2-oxazine was treated with methanesulfenyl bromide to produce the 5-bromo derivative as the methyl disulfide. Treatment of the 5-bromo derivative with sodium acetate produces the corresponding acetate which, after reductive cleavage of the acetate and reduction of the disulfide with sodium borohydride provides the required 4-thio-5-hydroxy dihydrooxazine as a mixture of stereoisomers.

Working Example III

Treatment of Patient with Chronic Hypertension with 4

A 60 year old male being treated with sodium iodide for hyperthyroidism has chronic hypertension (BP of 165/90). The patient is given 4 intravenously to maintain a blood concentration of 10 nanomolar. Blood pressure reduces to 140/85.

Working Example IV

Treatment of patient with chronic hypertension with 6 The patient who has chronic hypertension (BP of 165/90) is given 6 intravenously to maintain a blood concentration of 10 nanomolar. Blood pressure reduces to 140/85.

Variations

The foregoing description of the invention has been presented describing certain operable and preferred embodiments. It is not intended that the invention should be so limited since variations and modifications thereof will be obvious to the skilled in the art, all of which are within the spirit and scope of the invention.

What is claimed is:

1. A composition comprising N-(1-Cyanocyclohexyl)bicyclo[2.2.1]4-thio-5-hydroxy-3,6-dihydro-1,2-oxazine.

2. A composition comprising a compound of the following formula

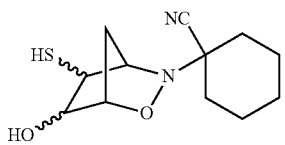

wherein H, S, O, N and C have their established meanings.

* * * * *